(12) United States Patent
Tsujita et al.

(10) Patent No.: US 7,179,221 B2
(45) Date of Patent: Feb. 20, 2007

(54) ENDOSCOPE UTILIZING FIDUCIARY ALIGNMENT TO PROCESS IMAGE DATA

(75) Inventors: Kazuhiro Tsujita, Kaisei-machi (JP); Yukihiro Nakajima, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 210 days.

(21) Appl. No.: 10/401,027

(22) Filed: Mar. 28, 2003

(65) Prior Publication Data
US 2004/0019253 A1 Jan. 29, 2004

(30) Foreign Application Priority Data
Mar. 28, 2002 (JP) ............................ 2002-092285

(51) Int. Cl.
*A61B 1/04* (2006.01)
*G06K 9/00* (2006.01)

(52) U.S. Cl. ..................................... 600/109; 382/128

(58) Field of Classification Search ................ 600/103, 600/109, 118, 168, 178; 348/65, 68, 74, 348/76; 382/128, 130
See application file for complete search history.

(56) References Cited

U.S. PATENT DOCUMENTS

| | | | | |
|---|---|---|---|---|
| 5,070,454 | A * | 12/1991 | Griffith | 378/163 |
| 5,697,885 | A * | 12/1997 | Konomura et al. | 600/109 |
| 6,724,922 | B1* | 4/2004 | Vilsmeier | 382/128 |
| 2002/0118867 | A1* | 8/2002 | Barfuss et al. | 382/128 |
| 2003/0210812 | A1* | 11/2003 | Khamene et al. | 382/128 |

* cited by examiner

*Primary Examiner*—John P. Leubecker
*Assistant Examiner*—Philip R. Smith
(74) *Attorney, Agent, or Firm*—Sughrue Mion, PLLC

(57) ABSTRACT

A correcting portion of an endoscope subjects a reference image to a magnification correction process so that the distance between a first mark and a second mark within the reference image is substantially equal to the distance between a first mark and a second mark within a comparative image. Next, the corrected reference image is subjected to a rotation correction process so that the orientation of the second mark with respect to the first mark within the reference image is substantially equal to the orientation of the second mark with respect to the first mark image within the comparison image. Further, the corrected reference image is subjected to a brightness distribution correction process so that the brightness distribution thereof becomes equal to that of the comparison image. The display state of the reference image and comparison image are made substantially equal, comparative diagnosis is facilitated, and diagnostic efficiency is improved.

14 Claims, 10 Drawing Sheets

ENDOSCOPE UTILIZING FIDUCIARY ALIGNMENT TO PROCESS IMAGE DATA

BACKGROUND OF THE INVENTION

1. Field of the Invention

The present invention relates in general to an endoscope apparatus for obtaining image data based on the reradiated light generated from an observation portion upon the irradiation thereof with an excitation light, and in particular to an endoscope apparatus for obtaining image data of an observation area having at least two types of marks thereon.

2. Description of the Related Art

In the field of medicine, there are known endoscope apparatuses which utilize an imaging element such as a CCD or the like for converting an optical image to an electric signal which are used to obtain image data of an observation area. By displaying the images obtained by a CCD on a monitor or the like, these endoscope apparatuses feature the advantage of enabling simultaneous observation of the image by a plurality of people. In addition, by subjecting an obtained image to various image processes before displaying said image, characteristics of the image can be enhanced so that an image also including changes in tissue structures not visible to the naked eye can be displayed on a monitor, making a great contribution to the advancement of medicine.

In recent years, much progress has been made in development efforts relating to the memory apparatuses with which theses types of endoscope apparatuses are equipped. As a result, it has become a common practice to store obtained image data in an internal or external memory, and when an image of the same portion is again obtained and displayed, the previously obtained image data of the same portion is read out and displayed so that a comparative diagnostic reading both of the images can be performed. This type of comparative diagnosis is oftentimes performed in regard to ascertaining the change occurring over time in a diseased portion, in particular, when medication or other treatment is being administered.

When displaying images on a monitor or the like to perform this type of comparative diagnosis, it is desirable that the display state of the vicinity of the diseased portion, e.g. the magnification, display angle and the like, of the previously obtained image data (hereafter referred to as reference image data) should match that of the presently obtained image data (hereafter referred to as comparison image data), so as to improve the accuracy of the diagnosis.

However, when an image is to be obtained using an endoscope apparatus, in view of the complexity of the form of the vicinity of the observation area, and the variance in the direction of expansion of a body cavity, there are cases in which the form of the observation area itself is different, whereby it is difficult to obtain a comparison image data of the same form as that obtained when the reference images data was obtained.

For example, if the distance between the scope portion of the endoscope apparatus and the observation area differs when the reference image data and the comparison image data are obtained, the magnification rate of the reference image data and the comparative image data differ, and when these images are displayed on a monitor or the like, even if the size of the diseased portion is the same, different sized diseased portions are displayed. Further, if the rotational angle of the distal end of the scope portion of the endoscope apparatus is different when the reference image data and the comparison image data are obtained, the imaging (rotation) angle of the reference image data and the comparison image data differ, and when these images are displayed on a monitor or the like, even the same diseased is displayed having different display angles.

That is to say, because there are many cases in which the magnification or display angle of the displayed diseased portion of a reference image and comparison image used to perform a comparative diagnosis is different, it is difficult for the diagnostician to immediately provide the diagnosis. In particular, because it is difficult to compare the finer differences in the images, a problem arises in that when a detailed comparison is to be performed, the efficiency of the diagnosis is lowered. Further, though it is possible to manually adjust the magnification or display angle of the diseased portion, aside from requiring a cumbersome manual operation, it is very difficult to accurately match the display angle or magnification of the diseased portion by sight, leading to difficulty in performing a detailed comparison and lower diagnostic efficiency.

Further, if, for example, the imaging angle of the distal end of the scope portion of the endoscope apparatus with respect to the observation portion differs, the form of the portion obtained as the reference image data and the form of the portion obtained as a comparison image data differ. Therefore, when these image data are displayed on a monitor or the like, even if the form of the diseased portion is the same, diseased portions having different forms are displayed. Further, when the reference image and the comparison image are obtained, there are cases in which the form of the diseased portion changes due to elongation or the like of the tissue structure itself, whereby diseased portions having different forms are displayed in this case also, leading again to low diagnostic efficiency.

SUMMARY OF THE INVENTION

The present invention has been developed in consideration of the forgoing circumstances, and it is an object of the present invention to provide an endoscope apparatus capable of improving the diagnostic efficiency when a reference image data and a comparison image data are used to perform a comparative diagnosis.

The endoscope apparatus according to the present invention is an endoscope apparatus comprising: a light emitting source for projecting light onto an observation area, and an imaging means for obtaining image data based on the reradiated light emitted from the observation area upon the irradiation thereof by the light projected from the light source; further comprising a memory means for storing as first image data obtained by projecting light onto an observation area to which a first mark and a second mark differing from said first mark have been applied; and a magnification correcting means for comparing the first image data stored in said memory means to second image data, which has been obtained after the passage of a predetermined period of time following the obtainment of said first image data, by projecting the light onto the observation area to which the first mark and the second mark have been attached, and subjecting at least one of the first image data and the second image data to a magnification correction process so that the distance between the first mark image data and the second mark image data within the first image data is substantially equal to the distance between the first mark image data and the second mark image data within the second image data.

Here, "reradiated light" refers to the light emitted from the observation area upon the irradiation thereof with the light projected from the light source. More specifically, the "reradiated light" refers to: fluorescence emitted from the observation area, the reflected light reflected from the observation area, or the dispersed light emitted after light has been dispersed at the surface of the observation area. Further, the marks are attached in advance in the vicinity of the diseased portion that is the object of the comparative diagnosis.

Another endoscope apparatus according to the present invention is an endoscope apparatus comprising: a light emitting source for projecting light onto an observation area, and an imaging means for obtaining image data based on the reradiated light emitted from the observation area upon the irradiation thereof by the light projected from the light source; further comprising a memory means for storing as first image data image data obtained by projecting light onto an observation area to which a first mark and a second mark differing from said first mark have been applied; and an orientation correcting means for comparing the first image data stored in said memory means to second image data, which has been obtained after the passage of a predetermined period of time following the obtainment of said first image data, by projecting the light onto the observation area to which the first mark and the second mark have been attached, and subjecting at least one of the first image data and the second image data to a rotation correction process so that the orientation of the second mark image data with respect to the first mark image data within the first image data is substantially equal to the orientation of the second mark image data with respect to the first mark image data within the second image data.

Here, the first mark and the second mark are applied in advance in the vicinity of the diseased portion or the like that is the object of the comparative diagnosis. Further, it is preferable that first mark and the second mark be applied in advance to the observation area so that the straight line connecting the first mark and the second mark passes substantially through the center of the diseased portion or the like. Still further, "the orientation of the second mark image data with respect to the first mark image data" refers to the direction along the line of sight from the first mark image data to the second mark image data.

Yet another endoscope apparatus according to the present invention is an endoscope apparatus comprising: a light emitting source for projecting light onto an observation area, and an imaging means for obtaining image data based on the reradiated light emitted from the observation area upon the irradiation thereof by the light projected from the light source; further comprising a memory means for storing as first image data image data obtained by projecting light onto an observation area including a specified area delimited by a first mark, a second mark, and a third mark, and a form correcting means for comparing the first image data stored in said memory means to second image data obtained by projecting the light onto said observation area including the specified area after the passage of a predetermined period of time from the obtainment of said first image data, and subjecting at least one of the specified area image data of the first image data and the specified area image data of the second image data to a form correcting process so that the form of the specified area within the first image data is substantially equal to the form of the specified area within the second image data.

Note that the three or more marks can be applied to the observation area. However, it is preferable that the diseased portion or the like that is the object of the comparative diagnosis is contained within the polygon formed by the all of the marks.

Further, the above-described endoscope apparatus can further comprise a rotation correcting means for subjecting at least one of the specified area image data within the first image data and the specified area image data within the second image data to a rotation correcting process so that the orientation of the second mark image data with respect to the first mark image data within the first image data that has been subjected to the form correction processing substantially matches the orientation of the second mark image data with respect to the first mark image data within the second image data that has been subjected to the form correction processing.

Still further, each of the above-described endoscope apparatuses can further comprise a brightness distribution correcting means for correcting the brightness of at least one of the two image data that have been subjected to the correction processing so that the brightness distribution of said two image data becomes substantially equal.

In addition, each of the above-described endoscope apparatuses can further comprise a diagnostic image forming means for forming a diagnostic image by performing a computational process between the two images that have been subjected to the correction processing.

The diagnostic image forming means can further comprise a superposed diagnostic image forming means for making one of the two correction processed image data semitransparent image data, and superposing said semitransparent image data on the other of the two correction processed image data to form superposed diagnostic image data.

Further, the diagnostic image forming means can further comprise an outline superposed diagnostic image forming means for judging, based on at least one of the two correction processed image data, the region of the diseased portion within said image data and forming outline image data composed of the outline of the judged diseased region, and superposing said outline image data over the other of the two correction processed image data to form outline superposed diagnostic image data. Note that it is preferable that the mark image positions within each of the respective images are matched when the two images are superposed.

Still further, the diagnostic image forming means can further comprise a difference diagnostic image forming means for forming, based on the difference between the corresponding pixels of the two correction processed image data, difference diagnostic image data. Note that "corresponding pixels" refers to the pixels residing at substantially the same positions within the respective images when the mark image positions of the respective images are in a substantially matched relationship.

If the illumination light source is a light source that projects an excitation light having a wavelength in the 400–420 nm range onto the observation area, the image obtaining means can also be a means for obtaining a fluorescence image of the fluorescence emitted from the observation area upon the irradiation thereof by the excitation light. Note that at least one of the first image data and the second image data can be obtained as fluorescence image data.

Further, each of the marks can be formed by a bioadhesive. If a fluorescence endoscope is to be used, it is preferable that the marks be formed by an adhesive or the like containing fluorophores.

Note that each correcting means can be a means that rerecords the processed image data before outputting the processed image data, or a means that directly outputs the processed image data to a monitor or external device without rerecording the processed image data.

According to the endoscope apparatus of the present invention, by comparing first image data, which has been stored in a memory means, of an observation area to which a first mark and a second mark have been applied and second image data obtained of the observation area after the passage of a predetermined period of time following the obtainment of said first image data, and further providing a magnification correcting means for subjecting at least one of the first image data and the second image data to a magnification correction process so that the distance between the first mark image data and the second mark image data within the first image data is substantially equal to the distance between the first mark image data and the second mark image data within the second image data, when the processed first image data and the processed second image data are displayed on a monitor or the like, the display magnification of the first image and the second image become substantially equal, whereby the comparison of both images becomes easy, leading to an improvement in the efficiency when performing a comparative diagnosis.

According to another endoscope apparatus of the present invention, by comparing first image data, which has been stored in a memory means, of an observation area to which a first mark and a second mark have been applied and second image data obtained of the observation area after the passage of a predetermined period of time following the obtainment of said first image data, and further providing an orientation correcting means for subjecting at least one of the first image data and the second image data to a rotation correction process so that the orientation of the second mark image data with respect to the first mark image data within the first image data is substantially equal to the orientation of the second mark image data with respect to the first mark image data within the second image data, when the processed first image data and the processed second image data are displayed on a monitor or the like the display angle of the first image and the second image become substantially equal, whereby the comparison of both images becomes easy, leading to an improvement in the efficiency when performing a comparative diagnosis.

According to yet another endoscope apparatus of the present invention, by comparing first image data, which has been stored in a memory means, of an observation area including a specified area delimited by a first mark, a second mark, and a third mark and second image data obtained of the observation area after the passage of a predetermined period of time following the obtainment of said first image data, and further providing a form correcting means for subjecting at least one of the specified area image data of the first image data and the specified area image data of the second image data to a form correcting process so that the form of the specified area within the first image data is substantially equal to the form of the specified area within the second image data, when the processed first image data and the second image data are displayed on a monitor or the like the display form of the specified area of the first image and the display form of the specified area of the second image become substantially equal, whereby the comparison of both specified area images becomes easy, leading to an improvement in the efficiency when performing a comparative diagnosis.

Further, if a rotation correcting means for subjecting at least one of the specified area image data within the first image data and the specified area image data within the second image data to a rotation correcting process so that the orientation of the second mark image data with respect to the first mark image data within the first image data that has been subjected to the form correction processing substantially matches the orientation of the second mark image data with respect to the first mark image data within the second image data that has been subjected to the form correction processing is provided, the display angle becomes substantially equal, in addition to the form displayed within the specified area of the first image and the second image, whereby the comparison of both specified area images becomes easy, leading to an improvement in diagnostic efficiency.

Still further, there are cases, for example, in which the imaging angle of the distal end of the scope portion differs with respect to the observation area when the reference image and the comparative image are obtained, causing differences in the respective brightness distributions and changes in the brightness of the diseased portion that make the comparative diagnosis difficult to perform. However, by providing a brightness correcting means for subjecting the at least one of the two image data that have been subjected to the correction processing to a brightness distribution correction process, the brightness of the first image and the second image, or the brightness of the specified area within the first image and the specified area within the second image can be made substantially equal, whereby the coloring of both images can be easily compared.

In addition, if each of the above-described endoscope apparatuses further comprises a diagnostic image forming means for forming a diagnostic image by performing a computational process between the two images that have been subjected to the correction processing, the image data contained in the two images can be extracted into a single image data set to form diagnostic image data.

If the diagnostic image forming means further comprises: a superposed diagnostic image forming means for making one of the two correction processed image data semitransparent image data, and superposing said semitransparent image data over the other of the two correction processed image data to form superposed diagnostic image data; or an outline superposed diagnostic image forming means for judging, based on at least one of the two correction processed image data, the region of the diseased portion within said image data and forming outline image data composed of the outline of the judged diseased region and superposing said outline image data over the other of the two correction processed image data to form outline superposed diagnostic image data; or a difference diagnostic image forming means for forming, based on the difference between the corresponding pixels of the two correction processed image data, difference diagnostic image data, the respective obtained image data can be displayed on a monitor and the comparative diagnosis performed by observing only a single image, whereby the diagnostic efficiency can be improved.

Further, if a light source for projecting an excitation light having a wavelength in the 400–420 nm range onto the observation area is used as the illumination light source, and a means for obtaining a fluorescence image of the fluorescence emitted from the observation area upon the irradiation thereof by the excitation light is used as the image obtaining means, by displaying the image obtained thereby on a monitor, the comparison diagnosis can be performed based on a fluorescence image reflecting the tissue state of a target subject.

Note that if each of the marks is formed by a bio-adhesive, it becomes easy to apply marks to living tissue. Further, if a fluorescence endoscope apparatus is used as the endoscope apparatus and the marks are formed by an adhesive or the like containing fluorophores, the mark image data become easy to distinguish in the fluorescence image data, and the mark images become readily visible on the fluorescence image.

DESCRIPTION OF THE PREFERRED EMBODIMENTS

Figure 1:
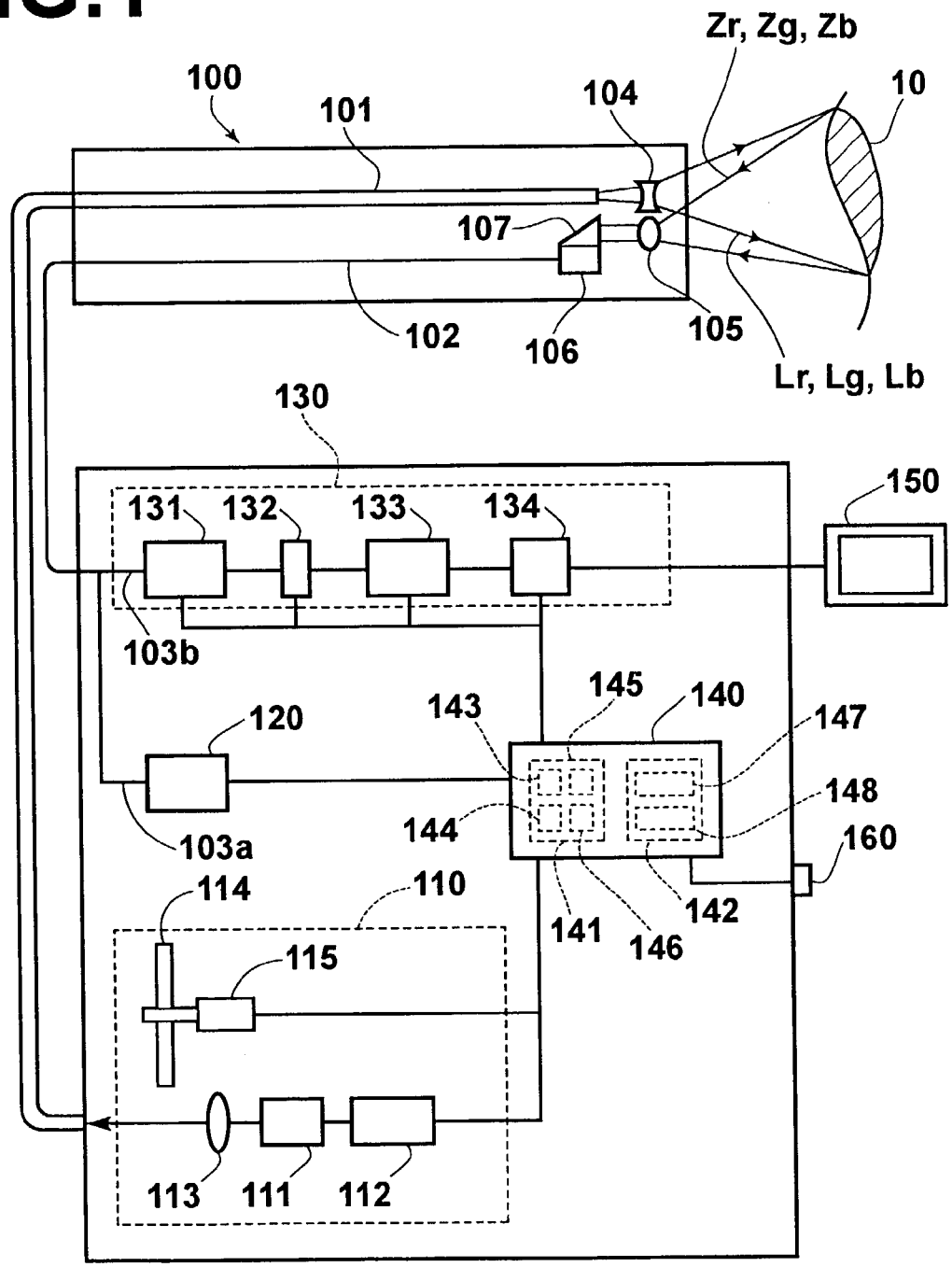
FIG. 1 is a schematic drawing of an endoscope apparatus according to the first embodiment of the present invention.

Hereinafter the preferred embodiments of the present invention will be explained with reference to the attached drawings. First, with reference to FIG. 1, an endoscope apparatus according to the first embodiment of the present invention will be explained. FIG. 1 is a schematic drawing of the endoscope apparatus of the current embodiment. The fluorescence endoscope apparatus according to the first embodiment is a sequential type endoscope apparatus that: projects R (red) light Lr, G (green) light Lg and B (blue) light Lb sequentially onto an observation area of a living tissue; images, by use of a CCD imaging element provided at the distal end of the endoscope, the light reflected from the observation area; and displays the image data of the observation as a color image on a monitor; wherein, when a reference image, which is first image data that has been previously obtained, is compared to a comparison image, which is second image data that has been obtained after the passage of a predetermined period of time following the obtainment of said reference image data, the endoscope apparatus subjects the reference image to a magnification correction process, a rotation correction process and a brightness correction process so that the display state of the reference image and the display state of the comparison image are substantially equal, then displays both images on the monitor. Note that when both images are displayed on the monitor, it is possible to select a desired display mode from among a side-by-side mode wherein the images are displayed next to each other, a superposed mode wherein the reference image is made a semitransparent image and superposed on the comparison image, and an outline superposed mode wherein the outline of the diseased portion of the reference image is superposed on the comparison image.

The fluorescence endoscope apparatus according to the first embodiment of the present invention comprises: a scope portion 100 which is provided with a CCD imaging element at the distal end thereof, for insertion into the primary nidus and suspected diseased areas in a body cavity of a patient; an illumination unit 110 that serves as the light emitting means for emitting the illuminating light, a CCD driver 120 for controlling the operation of the CCD imaging element, a standard image processing unit 130 for performing the process required for displaying an obtained image as a color image; a controller 140 for controlling the operation timing, the correction processing when a comparison diagnosis is to be performed, or the display processing and the like, a monitor 150 for displaying an obtained image, and an input portion 160 for inputting various settings.

The scope portion 100 is provided with a light guide 101 and a CCD cable 102 extending internally to the distal end thereof. An illuminating lens 104 and an objective lens 105 are provided at the distal end of the scope portion 100, further forward than the distal end of the light guide 101 and the CCD cable 102. A CCD imaging element 106 is provided at the distal end of the CCD cable 102, and a prism 107 is attached to said CCD imaging element 106.

The light guide 101 is connected to the illumination unit 110. A drive line 103a for transmitting the drive signal of the CCD imaging element 106 and an output line 103b that reads out the image signal from the CCD imaging element 106 are combined in the CCD cable 102. The CCD driver 120 is connected to one end of the drive line 103a. One end of the output line 103b is connected to the standard image processing unit 40.

The illumination unit 110 comprises: a white light source 111 formed of a xenon lamp that emits a white light; a light source power source 112 electrically connected to said white light source 111; a switching filter 114 for sequentially switching between R light Lr, G light Lg and B light Lb; and a filter rotating means 115 for rotating the switching filter 114.

Figure 2:
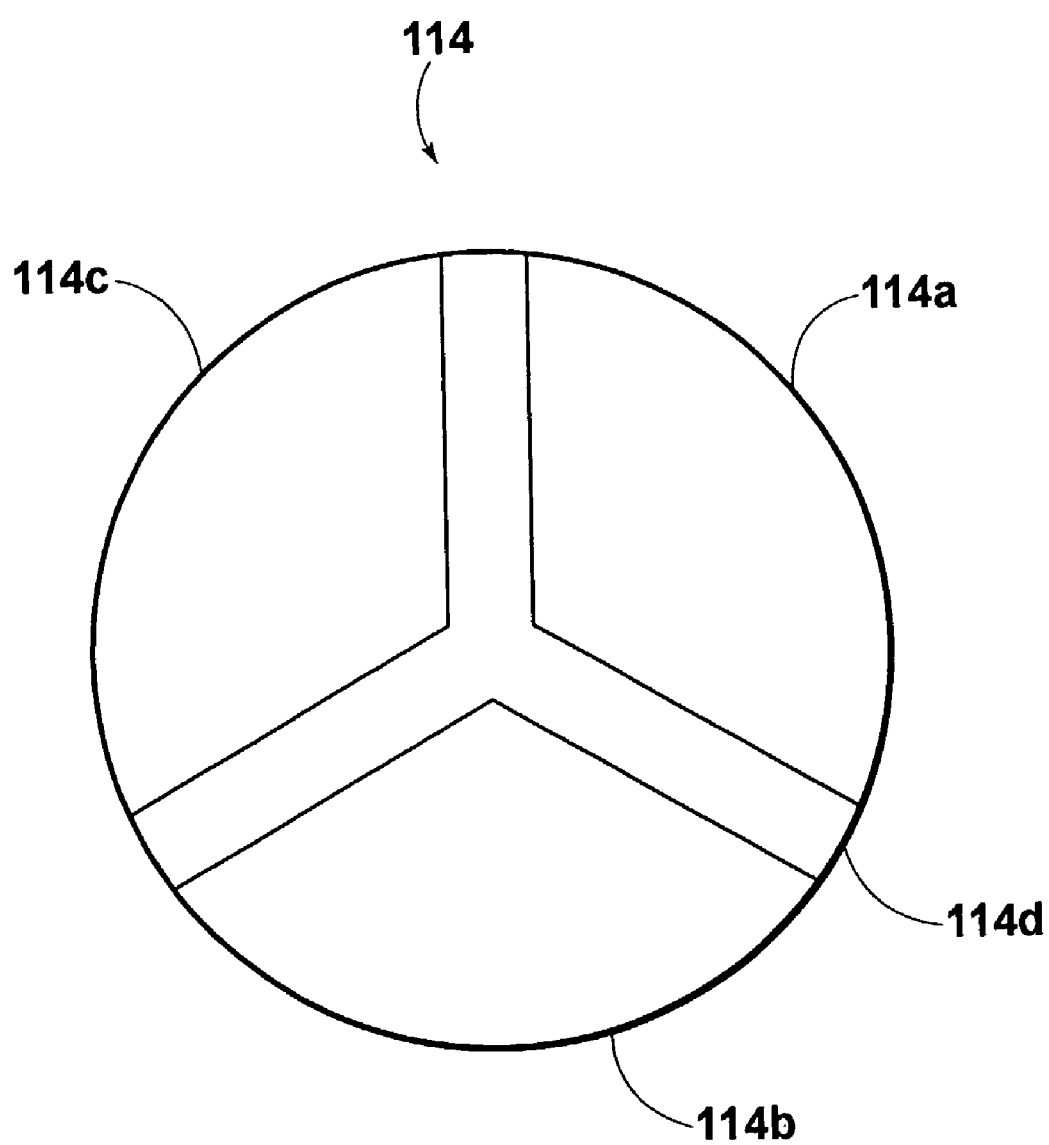
FIG. 2 is schematic drawing of the configuration of a switching filter.
Figure 3:
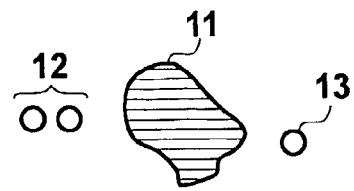
FIG. 3 is an illustration of a diseased portion and marks.

As shown in FIG. 2, the switching filter 114 is formed of an R filter 114a that transmits R light Lr, a G filter 114b that transmits G light Lg, a B filter 114c that transmits B light Lb, and a mask portion 114d having a light shielding function. The mask portion 114d serves to transmit the signal charge from the light receiving portion of the CCD imaging element 106 to the accumulation portion when the sequential light (R light Lr, G light Lg and B light Lb) is not being emitted.

The CCD driver 120 is a means that outputs control signals for controlling the timing of the CCD imaging element 106.

The standard image processing unit 130 comprises: a signal processing circuit 131 for processing the image signal received by the CCD imaging element 106; an AD conversion circuit 132 for digitizing the signal outputted from the signal processing circuit 131; an image memory 133 for storing the digitized image data of each color (a R image, a G image, and a B image) image; and a video signal processing portion 135 for converting the standard image signal outputted from the standard image signal processing means 131 to a video signal.

Note that the controller 140 is connected to each unit, and controls the operation timing thereof. Further, a correcting portion 141 for subjecting the reference image to correction processes, and a comparison display control portion 142 for controlling the display when comparison diagnoses are to be performed are provided. The correcting portion 141 is provided with a memory portion 143 for recording image data, a magnification correcting means 144 for subjecting reference image data to a magnification correction process, a rotation correcting portion 145 for subjecting reference image data to a rotation correction process, and a brightness correcting portion 146 for subjecting reference image data to a brightness correction process. The comparison display control portion 142 is provided with a superposed diagnostic image forming means 147 for forming superposed diagnostic images, and an outline superposed diagnostic image forming means 148 for forming outline superposed diagnostic images.

Next, the operation of the endoscope apparatus of the first embodiment of the present invention will be explained. First, the operation for obtaining a reference image is explained. Before the image is obtained, the doctor inserts the scope portion 100 into a body cavity of the patient and positions the distal end of the scope portion 100 within close proximity of the observation area 10. Note that according to the current embodiment, a first mark 12 and a second mark 13 are applied in the vicinity of a diseased portion 11 within the observation area 10. The first mark 12 and the second mark 13 have been applied in the vicinity of the diseased portion 11 in advance during a previous endoscopy, and are formed by a harmless bio-adhesive mixed with a white coloring agent, e.g. Tisseel™ or Beriplast™, which are cyano acrylate type surgical adhesives, or the like, wherein the first mark 12 is formed of two points and the second mark 13 is formed of one points. Further, Histoacryl Blue™ or Aron Alpha-A™ can also be used as the bio-adhesive.

The explanation will proceed starting with the operation for obtaining the R image. The white light source power source 112 is activated based on a signal from the controller 140, and white light is emitted from the white light source 111. The white light is focused by a focusing lens 113, and transmitted by the switching filter 114. In the switching filter 114, the R filter 114a is disposed in the light path based on a signal from the controller 140. Therefore, the white light becomes R light when transmitted by the switching filter 114. The R light enters the light guide 101, is guided to the distal end of the scope portion 100, and then projected onto the observation area 10 by the illuminating lens 104.

The R light Lr reflected from the observation area 10 is focused by the focusing lens 105, reflected by the prism 107, and focused on the CCD imaging element 106 as an R light reflectance image Zr.

The CCD imaging element 106 receives and photoelectrically converts the reflectance image Zr and outputs an electric signal corresponding to the variations in the intensity of the light forming the reflectance image Zr. The reflectance image Zr outputted from the CCD imaging element 106 is processed by the signal processing circuit 131 of the standard image processing unit 130, and outputted as processed R image signal data. The R image signal is digitized by the AD conversion circuit 132, and stored in the R image data memory region of the image memory 133.

Then, each time the predetermined time interval elapses, the G filter 114b is disposed on the light path, followed by the B filter 114c, sequentially, so as to obtain the G image and the B image according the same procedure as that described above for the R image. The G image and B image are then stored in the respective G image and B image memory regions of the image memory 133.

When the three color image data (hereafter referred to as RGB image data) has been recorded in the image memory 133, the video signal processing circuit 405 converts the RGB image data, which is outputted thereto in synchronization with the display timing, to a video signal and outputs the video signal to the monitor 50 for display as a color image.

Figure 4:
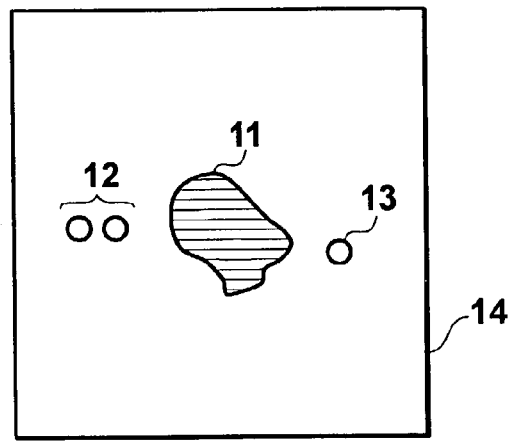
FIG. 4 is an illustration of a reference image.

While observing the displayed color image, the diagnostician adjusts the position of the distal end of the scope portion 100 so that the first mark 12 and the second mark 13 are displayed at an appropriate size in approximately the center of the image. When a desired image, such as that shown in FIG. 4, is displayed, the diagnostician operates the input portion 160 to issue a command to record a reference image data. Upon input of this command, the controller 140 records the RGB color image data of the color image displayed on the monitor 150 in the recording portion 143. At this time, specific information that can be appended to this image data, e.g. the patient's name, name of the imaged portion, image obtainment date or the like can be recorded together with the RGB image data.

Subsequent to the recording of the reference image data according to the above-described operation, an endoscopy is again performed with respect to the same portion of the same patient. The diagnostician again inserts the scope portion 100 into the body cavity of the patient and guides the distal end of the scope portion 100 to the vicinity of the observation area 10 to which the first mark 12 and the second mark 13 have been appended. Then, by performing the same operation described above for obtaining the reference image, the diagnostician obtains image data of the observation portion 10 and displays the obtained image data on the monitor 150 as a color image.

Figure 5:
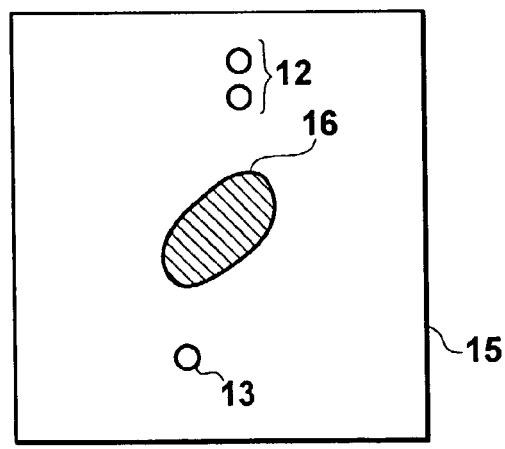
FIG. 5 is an illustration of a comparison image.

When the color image of the diseased portion 16 of the observation area 10 to which the first mark 12 and the second mark 13 have been appended is displayed, the diagnostician adjusts the position of the distal end of the scope portion 100 so that the first mark 12 and the second mark 13 are displayed at an appropriate size in approximately the center of the image. When the desired color image (hereafter referred to as a comparison image 15), such as that shown in FIG. 5, is displayed, the diagnostician operates the input portion 160 to issue a command to record comparison image data. Upon input of this command, the controller 140 reads out from the image memory 133 the RGB image data of the color image displayed on the monitor 150 and records the read out RGB color image data in the recording portion 143. At this time, specific information that can be appended to this image data, e.g. the patient's name, name of the imaged portion, image obtainment date or the like can be recorded together with the RGB image data.

When the diagnostician specifies, via the input portion 160, the comparison diagnosis command, the correcting portion 141 reads out, based on the appended data of the comparison image data 15, the reference image 14 from the recording portion 143.

Figure 6A:
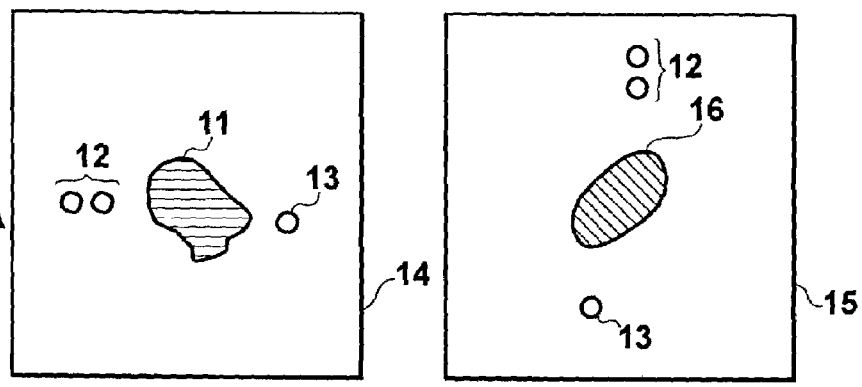
FIGS. 6A, 6B and 6C are illustrations of a reference image, a corrected reference image, and a comparison image, respectively.

Note that due to the effect of the medication administered, the size of the diseased portion 16 has been reduced compared to that of the diseasedportion 11; however, as shown in FIG. 6A, because the magnification of the comparison image 15 is larger of the that of the reference image 14, even if the reference image 14 and the comparison image 15 are observed and compared, it is difficult to readily recognize the contraction of the diseased portion.

The diagnostician specifies the display mode at the same time the input of the comparison diagnosis command is performed. A desired display mode can be selected from among: a side-by-side mode wherein both of the images are displayed next to each other; a superposed mode wherein the reference image is made a semitransparent image and superposed on the comparison image; and an outline superposed mode wherein the outline of the diseased portion of the reference image is superposed on the comparison image.

Figure 6B:
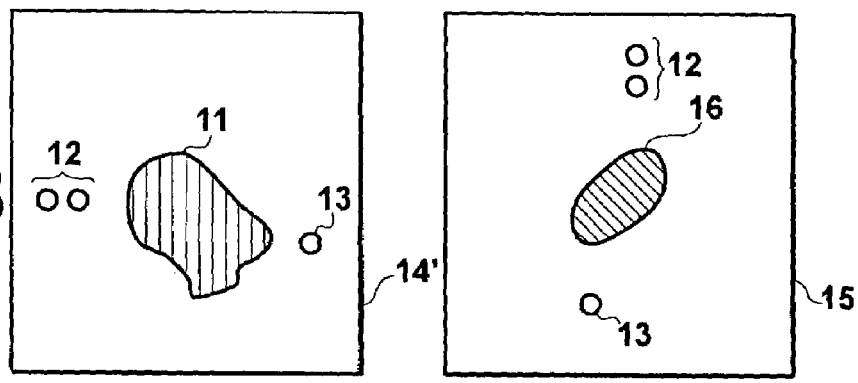

Upon input of the aforementioned command, the correcting portion 141 of the controller 140 initially performs a magnification correction process using the magnification correcting portion 144. First, the first mark image data obtained of the first mark and the second mark image data obtained of the second mark are discriminated, based on the color distribution of the comparison image data, and the distance between the first mark image data and the second mark image data (hereafter referred to as the inter-mark distance) is obtained by calculation. In the same fashion, the first mark image data and the second mark image data of the reference image data are discriminated and the distance therebetween calculated. Then, the magnification of the reference image data is corrected so that the inter-mark distance of the comparison image and the inter-mark distance of the reference image data become substantially equal, and the magnification corrected reference image data is stored as a corrected reference image data in the recording portion 143. At this time, if the comparison image data and the corrected reference image data are displayed, images such as those shown in FIG. 6B are displayed.

Next, the orientation correction portion 145 performs a rotation correction process. The orientation between the first mark image data and the second mark image data (hereafter referred to as the inter-mark orientation) of the comparison image data and the inter-mark orientation of the corrected reference image data are obtained by calculation. Then, the marks of the corrected reference image data are rotated so that the inter-mark orientation of the comparison image and the inter-mark orientation of the reference image data become substantially equal, and the corrected reference image data obtained thereby is rerecorded in the recording portion 143. Note that the orientation between the first mark image data and the second mark image data refers to the angle between the first mark image data and the second mark image data relative to the plane of the images when the images are displayed on a monitor or the like. For example, if the orientation of the first mark image with respect to the plane of the image is designated as 0 degrees, the orientation can be obtained by measuring the angle of display of the second mark image in degrees in the clockwise direction from the first mark image.

The final correction process is a brightness correction process performed by the brightness correcting portion 146. The brightness correcting portion 146 calculates the brightness distribution of the comparison image data and the corrected reference image data, then subjects the corrected reference image to a Y correction process, a contrast process or the like so that the brightness distribution of the comparison image data and the brightness distribution of the corrected reference image data become substantially equal, and rerecords the corrected reference image data in the recording portion 143.

Figure 6C:
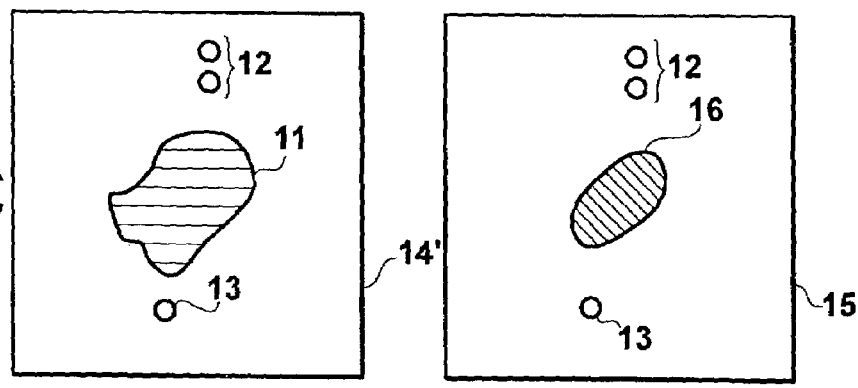

Next, the explanation will proceed starting with the case wherein the side-by-side display is selected as the display mode. The comparison display control portion 142 outputs the comparison image data and the corrected reference image data stored in the recording portion 143 to the video signal processing circuit 134. Both image data are converted to video signals, outputted to the monitor 150, and displayed as a corrected reference image 14' and a comparison image 15 as shown in FIG. 6C. By observing and comparing the corrected reference image 14' and the comparison image 15, the diagnostician can easily recognize the contraction in the size of the diseased portion 16 compared to that of the diseased portion 11.

Figure 7A:
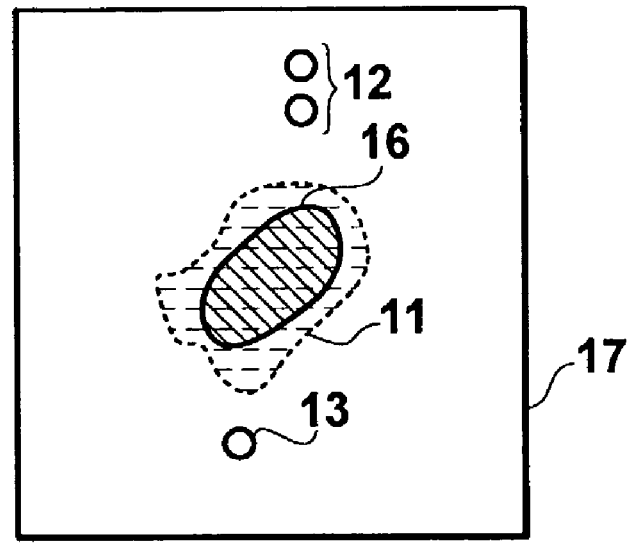
FIGS. 7A and 7B are illustrations of a superposed diagnostic image and an outline superposed image, respectively.

For the case wherein the superposed display mode is selected, the superposed diagnostic image forming portion 147 first reads out the corrected reference image data 14' and the comparison image data 15 from the recording portion 143, makes the corrected reference image data 14' a semitransparent image, and superposes the semitransparent corrected reference image data on the comparison image data 15 to form a superposed diagnostic image data. Note that when superposing the image data, the image data are superposed so that the positions of the first mark image data and the second mark image data within the comparison image data and the positions of the first mark image data and the second mark image data within the semitransparent corrected reference image data are substantially matched. The comparative display means 142 outputs the superposed diagnostic image data to the video signal processing circuit 134. The superposed diagnostic image data is converted to a video signal, output to the monitor 150 and displayed thereon as a superposed diagnostic image 17 as shown in FIG. 7A. By observing the displayed superposed diagnostic image 17, the diagnostician can easily recognize the contraction in the size of the diseased portion 16 compared to that of the diseased portion 11.

Figure 7B:
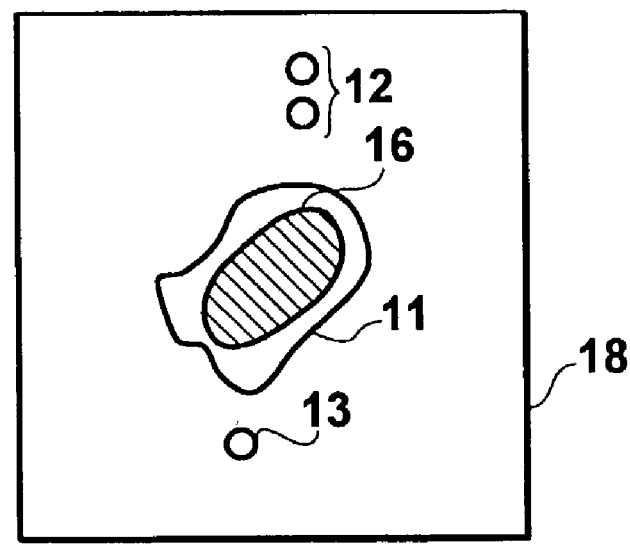

For the case wherein the outline superposed display mode is selected, the outline superposed diagnostic image forming portion 147 first reads out the corrected reference image data 14' and the comparison image data 15 from the recording portion 143. The outline superposed diagnostic image forming portion 147 judges, based on the color distribution or the like of the corrected reference image data 14', the diseased region, forms an outline image data composed of the outline of the diseased region, the first mark image data and the second mark image data, and superposes the outline image data on the comparison image data to form an outline superposed diagnostic image data. Note that when superposing the image data, the image data are superposed so that the positions of the first mark image data and the second mark image data within the comparison image data and the positions of the first mark image data and the second mark image data within the outline image data are substantially matched. The comparison display control portion 142 outputs the outline superposed diagnostic image data to the video signal processing circuit 134. The outline superposed diagnostic image data is converted to a video signal, output to the monitor 150 and displayed thereon as a superposed diagnostic image 18 as shown in FIG. 7B. By observing the displayed outline superposed diagnostic image 17, the diagnostician can easily recognize the contraction in the size of the diseased portion 16 compared to that of the diseased portion 11.

As elucidated in the forgoing explanation, according the endoscope apparatus of the present invention: first, the reference image data is subjected to a magnification correction process so that the inter-mark distance of the reference image data and the inter-mark distance of the comparison image data becomes substantially equal; next, the reference image data is subjected to a rotation correction process so that the inter-mark orientation of the reference image data and the inter-mark orientation of the comparison image data becomes substantially equal; further, the reference image data is subjected to a brightness distribution correction process so that the brightness distribution of the reference image data and the brightness distribution of the comparison image data becomes substantially equal to form a corrected reference image data; whereby, when the corrected reference image data and the comparison image data are displayed on a monitor or the like, because the magnification, orientation, and brightness distribution of the image of the vicinity of the diseased portion 11 displayed in the corrected reference image 14' and the diseased portion 16 displayed in the comparison image are substantially equal, comparison of both images becomes easy, and the diagnostic efficiency in performing a comparison diagnosis is improved.

Further, a difference display mode, wherein the degree of brightness of the pixels in the comparison image can be subtracted from the degree of brightness of the pixels corresponding thereto in the corrected reference image to obtain a difference value and a pseudo color assigned to the difference value to form a difference diagnostic image which is then displayed on a monitor or the like, can be further provided.

Note that when the comparison image 15 has been obtained, it is possible to perform only one or two of the correction processes from among the magnification correction process, the rotation correction process and the brightness distribution correction process, according to necessity. Further, although according to the forgoing explanation the reference image data has been subjected to the correction processes to render the display state of the reference image data and the comparison image data substantially equal, the current embodiment is not limited thereto; an endoscope apparatus that subjects the comparison image to the correction processes, or an endoscope apparatus that subjects both the reference image data and the comparison image data to the correction processes is also possible. Still further, when superposing the image data, the comparison image can be made transparent or the outline image data can be extracted from the comparison image data and superposed on the corrected reference image data.

Figure 8:
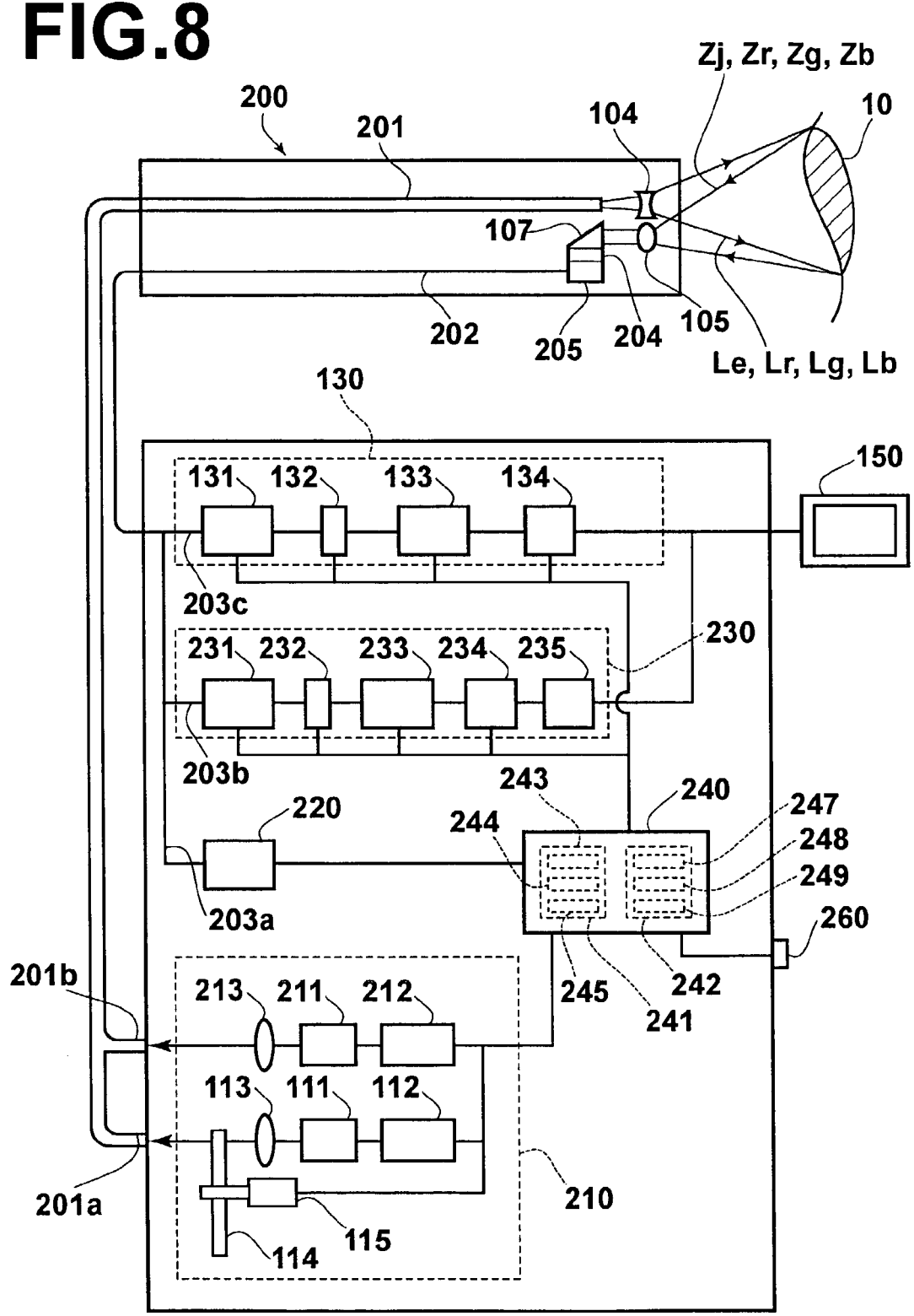
FIG. 8 is a schematic drawing of an endoscope apparatus according to the second embodiment of the present invention.
Figure 9:
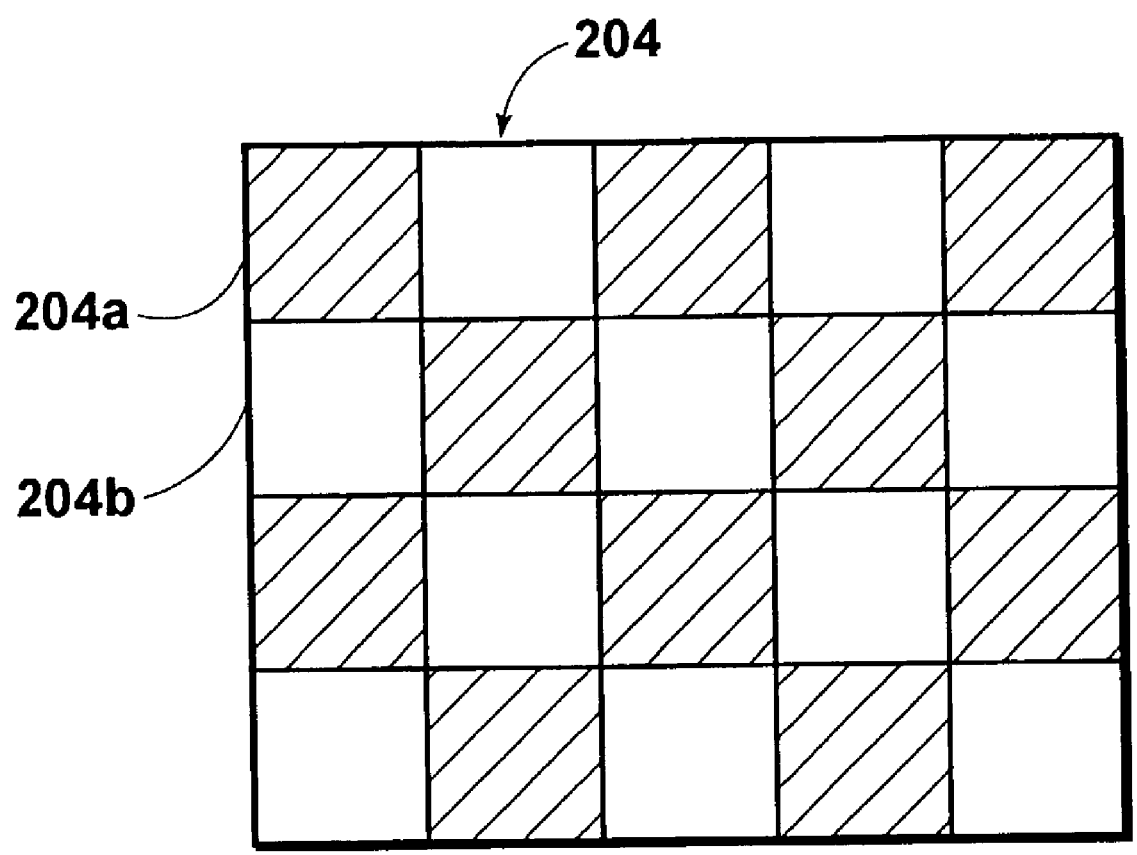
FIG. 9 is a schematic drawing of a mosaic filter.
Figure 10:
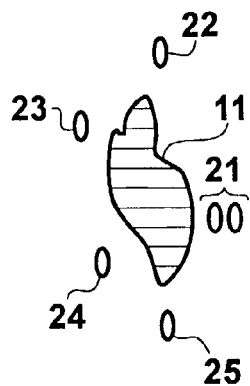
FIG. 10 is an illustration of a diseased portion and marks.

Next, a fluorescence endoscope apparatus according to the second embodiment of the present invention will b explained with reference to FIGS. 8 and 9. FIG. 8 is schematic drawing of the fluorescence endoscope apparatus according to the second embodiment of the present invention. Note that elements appearing in FIG. 8 that are common to FIG. 1 are likewise labeled, and further explanation thereof omitted so far as it is not particularly required.

The fluorescence endoscope apparatus according to the second embodiment of the present invention operates: a standard image mode, wherein R (red) light Lr, G (green) light Lg and B (blue) light Lb are projected sequentially onto an observation area of living tissue and the reflected light reflected from the observation area thereupon is imaged, by use of a CCD imaging element provided at the distal end of the endoscope, to obtain image data of the observation area, which is then displayed as a color image on a monitor; and a fluorescence diagnostic image mode, wherein an excitation light is projected onto an observation area of living tissue and the fluorescence light emitted from the observation area thereupon is imaged by use of the CCD imaging element provided at the distal end of the endoscope to obtain fluorescence image data of the observation area, which is fluorescence diagnostic image data corresponding to the relative ratios of signal intensities of predetermined wavelength ranges, displayed as a pseudo color image on a monitor. When a fluorescence diagnostic image is to be displayed, it is possible to compare the fluorescence diagnostic image with a reference image that has been obtained beforehand as a first image and a comparison image that has been obtained as a second image after the passage of a predetermined period of time following the obtainment of said reference image. When comparing the aforementioned images, in order to make the display state of the comparison image and the reference image substantially equal, the reference image is subjected to a form correction process and a rotation correction process, then both the corrected reference image and the comparison image are displayed on the monitor. Note that when the comparison image and the reference image are displayed on the monitor, it is possible to select a desired display mode from among a side-by-side mode wherein the images are displayed next to each other, a superposed mode wherein the reference image is made a semitransparent image and superposed on the comparison image, an outline superposed mode wherein the outline of the diseased portion of the reference image is superposed on the comparison image, and a difference mode wherein the relative ratio of the pixels of the comparison image are subtracted from the relative ratio of the corresponding pixels of the reference image to obtained the difference, and a difference diagnostic image, formed based on said difference, is displayed.

The fluorescence endoscope apparatus according to the second embodiment of the present invention comprises: a scope portion 200 which is provided with a CCD imaging element 205 at the distal end thereof, for insertion into the primary nidus and suspected diseased areas in a body cavity of a patient; an illumination unit 210, a CCD driver 220 for controlling the operation of the CCD imaging element, a standard image processing unit 130; a fluorescence image processing unit 230 for displaying a pseudo color image corresponding to the relative ratios of signal intensities of predetermined wavelength ranges of an imaged fluorescence image, a controller 240 for controlling the operation timing, the correction processing when a comparison diagnosis is to be performed, or the display processing and the like, a monitor 150 for displaying an obtained image, and an input portion 260 for inputting various settings.

The scope portion 200 is provided with a light guide 201 and a CCD cable 202 extending internally to the distal end thereof. An illuminating lens 104 and an objective lens 105 are provided at the distal end of the scope portion 100, further forward than the distal end of the light guide 201 and the CCD cable 202. The light guide 201 is formed as an integrated cable in which a light guide 201a for illumination light and a light guide 201b for excitation light are bundled, and each of said light guides is connected to the illuminating unit 210. A CCD imaging element 205 provided with an on-chip mosaic filter 204 formed of a plurality of microscopic bandwidth filters combined to form a mosaic pattern is provided at the distal end of the CCD cable 202, and a prism 107 is attached to said CCD imaging element 202.

The mosaic filter 204 is formed of narrow band filters 204a that transmit light having a wavelength in the 430–530 nm wavelength range and a wide band filters 204b that transmit light having a wavelength in the 430–700 nm wavelength range, which are alternately arranged in a mosaic pattern. Each of the band pass filters 204a and 204b is in a one-to-one correspondence with a pixel of the CCD imaging element 205.

The CCD cable 202 is formed as an integrated cable in which a drive line 203a for transmitting the drive signals of the CCD imaging element 205, and output lines 203b and 203c for reading out the signal charge from the CCD imaging element 205 are combined. One end of the drive line 203*a* is connected to the CCD driver 220; one end of the output line 203*b* is connected to the fluorescence image processing unit 230; and one end of the output line 203*c* is connected to the standard image processing unit 130.

The illumination unit 210 comprises: a white light source 111; a white light source power source 112; a focusing lens 113; a switching filter 114; a filter rotating means 115; a GaN type semiconductor laser 211; a semiconductor laser power source 212 electrically connected to said a GaN type semiconductor laser 211; and a focusing lens 213.

The CCD driver 220 is a means that outputs control signals for controlling the timing of the CCD imaging element 205.

The fluorescence image processing unit 230 comprises: a signal processing circuit 231 for processing the image signal received by the CCD imaging element 205; an AD conversion circuit 232 for digitizing the signal outputted from the signal processing circuit 231; an image memory 233 for storing the digitized image data corresponding to each optical filter of the mosaic filter 204; a fluorescence image forming circuit 234 for forming fluorescence image data, which is a pseudo color image data, from the narrow wavelength range image signal that has passed through the narrow band filters 204*a* and the wide wavelength range image signal that has passed through the wide band filters 204*b*, which are stored in the image memory 233; and a video signal processing portion 235 for converting the fluorescence image signal outputted from the fluorescence image forming circuit 234 to a video signal and outputting the converted signal.

Note that the controller 240 is connected to each unit, and controls the operation timing thereof. Further, a correcting portion 241 for subjecting the reference image to correction processes, and a comparison display control portion 242 for controlling the display when comparison diagnoses are to be performed. The correcting portion 241 is provided with a memory portion 243 for recording image data, a form correcting portion 244 for subjecting reference image data to a form correction process, and a rotation correcting means 245 for subjecting reference image data to a rotation correction process. The comparison display control portion 242 is provided with a superposed diagnostic image forming portion 247 for forming superposed diagnostic images, an outline superposed diagnostic image forming portion 248 for forming outline superposed diagnostic images, and a difference diagnostic image forming portion 249 for forming difference diagnostic image data.

Next, the operation of the endoscope apparatus of the second embodiment of the present invention will be explained. Note that according to the current embodiment, the emission of the illumination light (Lr, Lg, Lb), the obtainment of the standard images (Zr, Zg, Zb), the emission of the excitation light Le, and the obtainment of the fluorescence image Zj are performed in a time division manner. The fluorescence image and the standard image can be displayed on the monitor concurrently, or only one of the image obtaining operations can be performed by a switching operation and either the fluorescence image or the standard image displayed on the monitor 150. The image processing for emitting the illumination light (Lr, Lg, Lb), obtaining the standard images (Zr, Zg, Zb), and displaying the standard image is the same as that occurring in the first embodiment, therefore, further explanation thereof is omitted. The operations for emitting the excitation light Le, obtaining the fluorescence image Zj, displaying the fluorescence diagnostic image, and performing the comparison of the fluorescence diagnostic images will be explained in detail.

Before the image is obtained, the doctor inserts the scope portion 200 into a body cavity of the patient and positions the distal end of the scope portion 200 within close proximity of the observation area 10. Note that according to the current embodiment, a first mark 21, a second mark 22, a third mark 23, a fourth mark 24 and a fifth mark 25 are applied in the vicinity of a diseased portion 11 within the observation area 10. The marks have been applied in the vicinity of the diseased portion 11 in advance during a previous endoscopy, and are formed by a harmless bio-adhesive mixed with a white coloring agent, e.g. Tisseel™ or Beriplast™, which are cyano acrylate type surgical adhesives, or the like, wherein the first mark 21 is formed of two points, the second mark 22 is formed of three points, and the third mark 23, the fourth mark 24 and fifth mark 25 are each formed of one point. Note that if it is preferable that the marks not be displayed on the standard image, a colorless bio-adhesive can be used, and for cases in which it is preferable that the marks are displayed on the standard image, a bio-adhesive having a conspicuous color when applied to living tissue can be used.

First, the operation for obtaining a reference image will be explained, followed by an explanation of the operations for obtaining a comparison image and for generating a corrected reference image. The excitation light power source 212 is activated, based on a signal from the controller 240, and the excitation light Le having a wavelength of 410 nm is emitted from the GaN type semiconductor laser 211. The excitation light Le is transmitted by a lens 213, enters the light guide 201, is guided to the distal end of the scope portion 200, and projected onto the observation area 1 from the illuminating lens 104.

The fluorescence emitted from the observation area 1 upon the irradiation thereof by the excitation light Le is focused by the focusing lens 105, reflected by the prism 107, transmitted by the mosaic filter 204, and focused on the CCD imaging element 205 as a fluorescence image Zj.

The signal outputted from the CCD imaging element 205 is processed by the signal processing circuit 231 of the fluorescence image processing unit 230, digitized by the AD conversion circuit 232, separated into a narrow band fluorescence image signal and a wide band fluorescence image signal, and stored in respective memory regions of the image memory 233. The fluorescence image forming circuit 234 calculates the ratio of the signal intensity of the image signal of the narrow wavelength band and the wide wavelength band for adjacent pixels (hereafter referred to as the signal intensity ratio), assigns color data, that is, a pseudo color to each pixel on the basis of the signal intensity ratio to form fluorescence image data, and outputs the formed fluorescence image data in conjunction with the display timing to the video signal processing circuit 235. The video signal processing circuit 235 converts the fluorescence image data to video signals and outputs the video signal to the monitor 150. The monitor 150 displays the fluorescence diagnostic image data, which is a pseudo color image.

Note that the fluorescence diagnostic image is a displayed as a pseudo color image whose display color changes in accordance with the variation in the relative ratio of the signal intensity of the wide band image signal and the signal intensity of the narrow band signal. It is preferable that the pseudo color be set so that the difference in the display color of the fluorescence emitted from a normal tissue and the fluorescence emitted from a diseased tissue is readily apparent. For example, by setting the pseudo colors so that the fluorescence emitted from a normal tissue can be displayed as white and the fluorescence emitted from a diseased tissue can be displayed as pink, the diagnostician can easily recognize the diseased portion.

Figure 11:
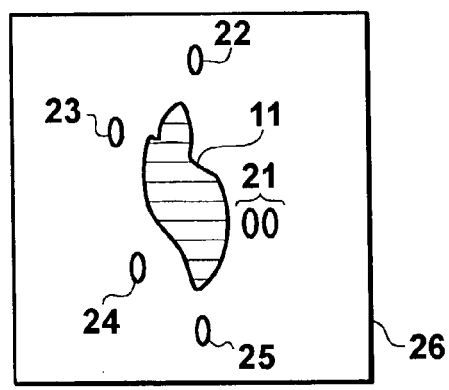
FIG. 11 is an illustration of a reference image.

While observing the displayed color image, the diagnostician adjusts the position of the distal end of the scope portion 200 so that the first mark 21 through the fifth mark 25 and the second mark 13 are displayed at an appropriate size in approximately the center of the image. When a desired image, such as that shown in FIG. 11, is displayed (hereafter referred to as a reference image 26), the diagnostician operates the input portion 260 to issue a command to record reference image data. Upon input of this command, the controller 240 records the fluorescence image data of the fluorescence image displayed on the monitor 150 in the recording portion 243 (hereafter referred to as a reference image data). At this time, specific information that can be appended to this image data, e.g. the patient's name, name of the imaged portion, image obtainment date or the like can be recorded together with the fluorescence image data.

Subsequent to the recording of the reference image data according to the above-described operation, an endoscopy is again performed with respect to the same portion of the same patient. The diagnostician again inserts the scope portion 200 into the body orifice of the patient and guides the distal end of the scope portion 200 to the vicinity of the observation area 10 to which the first mark 21 through the fifth mark 25 have been appended. Then, by performing the same operation described above for obtaining the reference image, the diagnostician obtains image data of the observation portion 10 and displays the obtained image data on the monitor 150 as a color image.

Figure 12:
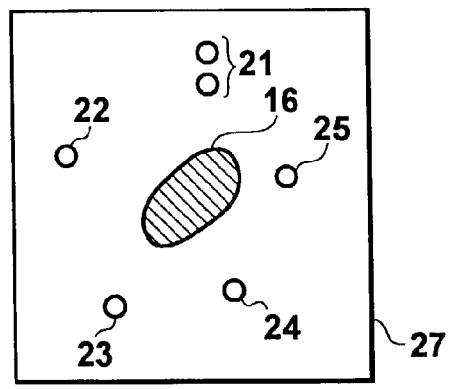
FIG. 12 is an illustration of a comparison image.

When the color image of the diseased portion 16 of the observation area 10 to which the first mark 21 through the fifth mark 25 have been appended is displayed, the diagnostician adjusts the position of the distal end of the scope portion 200 so that the first mark 21 through the fifth mark 25 are displayed at an appropriate size in approximately the center of the image. When the desired color image (hereafter referred to as a comparison image 27), such as that shown in FIG. 12, is displayed, the diagnostician operates the input portion 260 to issue a command to record comparison image data. Upon input of this command, the controller 240 reads out from the fluorescence image forming circuit 234 the fluorescence image data (hereafter referred to as a comparative image data) of the fluorescence diagnostic image displayed on the monitor 150 and records the read out fluorescence color image data in the recording portion 243. At this time, specific information that can be appended to this image data, e.g. the patient's name, name of the imaged portion, image obtainment date or the like can be recorded together with the fluorescence image data.

When the diagnostician specifies, via the input portion 260, the comparison diagnosis command, the correcting portion 241 reads out, based on the appended data of the comparison image data 27, the reference image 26 from the recording portion 243.

Figure 13A:
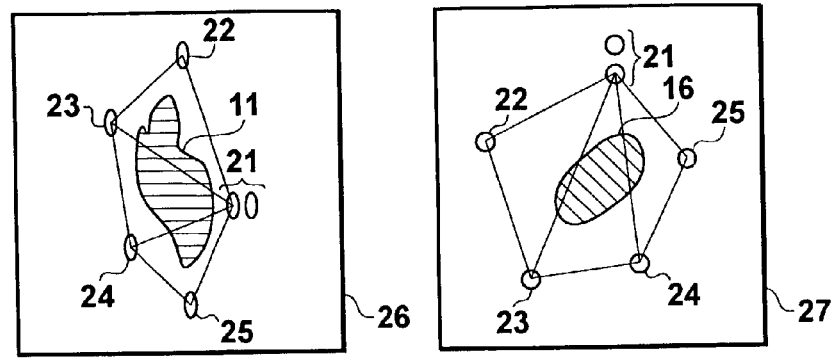
FIGS. 13A 13B and 13C are illustrations of a reference image, a corrected reference image, and a comparison image, respectively.

Note that due to the effect of the medication administered, the size of the diseased portion 16 has been reduced compared to that of the diseased portion 11; however, as shown in FIG. 13A, because the magnification of the comparison image 27 is larger than that of the reference image 26, even if the reference image 26 and the comparison image 27 are observed and compared, it is difficult to readily recognize the contraction of the diseased portion.

The diagnostician specifies the display mode at the same time the input of the comparison diagnosis command is performed. A desired display mode can be selected from among a side-by-side mode, a superposed mode, an outline superposed mode, and a difference mode.

Figure 13B:
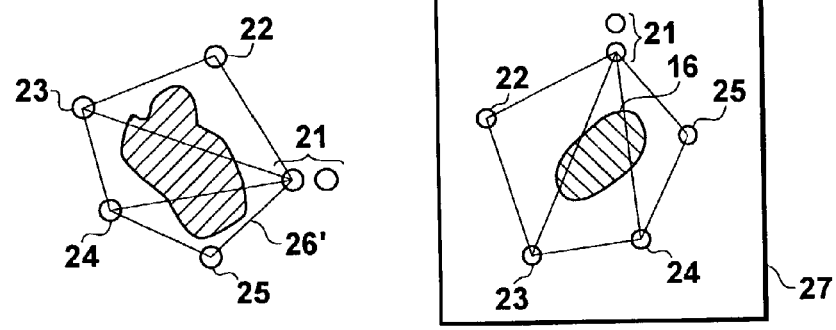

Upon input of the aforementioned command, the correcting portion 241 of the controller 240 initially performs a form correction process using the form correcting portion 244. First, the first mark image data through the fifth mark image data obtained of the first mark 21 through the fifth mark 25 are discriminated based on the color distribution of the comparison image data. Then, the triangular area enclosed between the first mark image data, the second mark image data and the third mark image data is subjected to the form correction process. When the form correction process is performed, the reference image data is subjected to the form correction process for correcting the form of a triangular area so that the inter-mark distance between the first mark image data, the inter-mark distance between the second and the third mark image data, and the inter-mark distance between the third mark image data and the first mark image data of the reference image are substantially equal to the inter-mark distance between the first mark image data, the inter-mark distance between the second and the third mark image data, and the inter-mark distance between the third mark image data and the first mark image data of the comparison image data. The form correction processing is performed in the same manner proceeding sequentially wherein the triangular area enclosed by the first mark image data, the third mark image data and the fourth mark image data and the triangular area enclosed by the first mark image data, the fourth mark image data and the fifth mark image data are subjected to form correction process to complete the form processing of the polygonal area image data to obtain a corrected reference data, which is then stored in the recording portion 243. If the corrected reference image data and the comparison image data are displayed at this point in time, the images will of the type shown in FIG. 13B. Note that because the form correction processing corrects only the area enclosed by each respective set of marks, only the area enclosed by each respective set of marks is displayed as a corrected reference image. The correction processing is to be performed so that the positional relationship of the area enclosed by each respective set of marks also becomes the same. For example, the center position in each area of both images can be obtained, and the form correction process performed so that the positional relationship therebetween becomes substantially equal.

Next, the orientation correction portion 245 performs a rotation correction process. The orientation between the first mark image data and the second mark image data (hereafter referred to as the inter-mark orientation) of the comparison image data and the inter-mark orientation of the corrected reference image data are obtained by calculation. Then, the marks of the corrected reference image data are rotated so that the inter-mark orientation of the comparison image and the inter-mark orientation of the reference image data become substantially equal, and the corrected reference image data obtained thereby is rerecorded in the recording portion 243. Note that when performing the rotation correction process, it is possible, for example, to obtain the center position of the area enclosed by all of the marks of the corrected reference image data and the center position of the area enclosed by all of the marks of the comparison image data, and to subject the corrected reference image data to a rotation process so that the orientation between the center position of the corrected reference image and the first mark image thereof becomes substantially equal to the orientation between the center position of the comparison image data and the first mark image thereof.

Figure 13C:
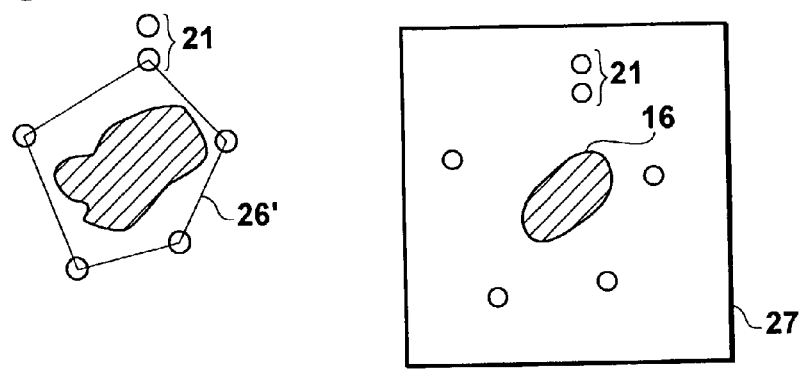

Next, the explanation will proceed starting with the case wherein the side-by-side display is selected as the display mode. The comparison display control portion 242 outputs the comparison image data and the corrected reference image data stored in the recording portion 243 to the video signal processing circuit 234. Both image data are converted to video signals, outputted to the monitor 150, and displayed as a corrected reference image 26' and a comparison image 15 as shown in FIG. 13C. By observing and comparing the corrected reference image 26' and the comparison image 27, the diagnostician can easily recognize the contraction in the size of the diseased portion 16 compared to that of the diseased portion 11.

Figure 14A:
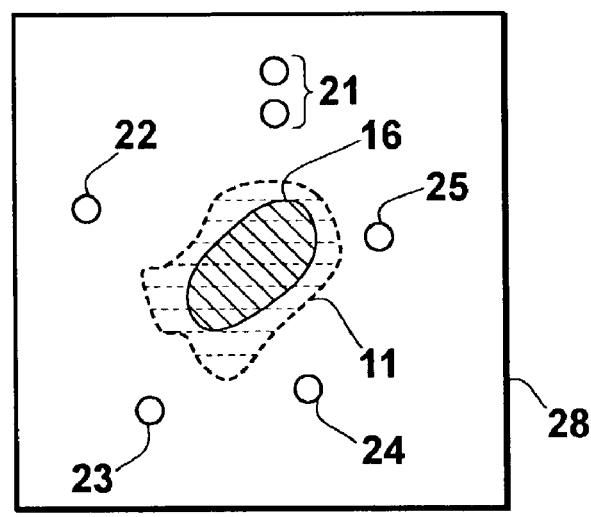
FIGS. 14A, 14B and 14C are illustrations of a superposed diagnostic image and an outline superposed diagnostic image.

For the case wherein the superposed display mode is selected, the superposed diagnostic image forming portion 247 first reads out the corrected reference image data 26' and the comparison image data 27 from the recording portion 243, makes the corrected reference image data 26' a semi-transparent image, and superposes the semitransparent corrected reference image data on the comparison image data 27 to form a superposed diagnostic image data. Note that when superposing the image data, the image data are superposed so that the positions of the first mark image data and the second mark image data within the comparison image data and the positions of the first mark image data and the second mark image data within the semitransparent corrected reference image data are substantially matched. The comparative display means 242 outputs the superposed diagnostic image data to the video signal processing circuit 235. The superposed diagnostic image data is converted to a video signal, output to the monitor 150 and displayed thereon as a superposed diagnostic image 28 as shown in FIG. 14A. By observing the displayed superposed diagnostic image 28, the diagnostician can easily recognize the contraction in the size of the diseased portion 16 compared to that of the diseased portion 11.

Figure 14B:
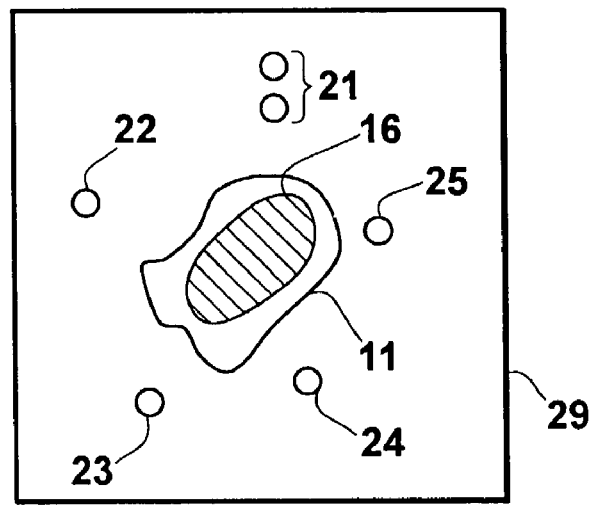

For the case wherein the outline superposed display mode is selected, the outline superposed diagnostic image forming portion 247 first reads out the corrected reference image data 267 and the comparison image data 15 from the recording portion 243. The outline superposed diagnostic image forming portion 247 judges, based on the color distribution or the like of the corrected reference image data 26', the diseased region, forms an outline image data composed of the outline of the diseased region, the first mark image data and the second mark image data, and superposes the outline image data on the comparison image data to form an outline superposed diagnostic image data. Note that when superposing the image data, the image data are superposed so that the positions of the first mark image data and the second mark image data within the comparison image data and the positions of the first mark image data and the second mark image data within the outline image data are substantially matched. The comparison display control portion 242 outputs the outline superposed diagnostic image data to the video signal processing circuit 235. The outline superposed diagnostic image data is converted to a video signal, output to the monitor 150 and displayed thereon as a superposed diagnostic image 18 as shown in FIG. 14B. By observing the displayed outline superposed diagnostic image 29, the diagnostician can easily recognize the contraction in the size of the diseased portion 16 compared to that of the diseased portion 11.

Figure 14C:
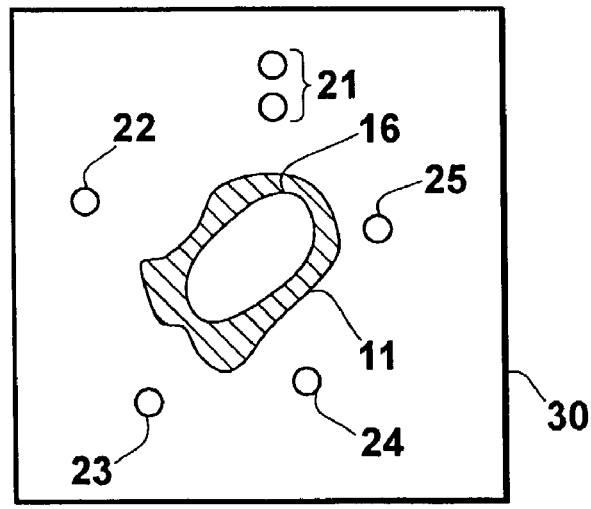

For the case wherein the difference display mode is selected, the difference diagnostic image forming portion 249 first reads out the corrected reference image data and the comparison image data from the recording portion 243. Next, the difference diagnostic image forming portion 249 shifts the pixel positions of the comparison image data so that the first mark image data and the second mark image data within the comparison image data substantially match the positions of the first mark image data and the second mark image data within the corrected reference image data. Then, the signal intensity of each pixel of the corrected reference image and the comparison image is reverse calculated from the pixel data (color data), the ratio of the signal intensity of the comparison image data is subtracted from the ratio of the signal intensity of the corrected reference image data, and the values obtained thereby are used to form the difference diagnostic image data, to which pseudo colors have been assigned. The comparison display control portion 242 outputs the difference diagnostic image data to the video signal processing circuit 235. The difference diagnostic image data is converted to a video signal, output to the monitor 150 and displayed thereon as a difference diagnostic image 30 as shown in FIG. 14C.

Note that the difference diagnostic image is a pseudo color image wherein the display color varies according to the difference of the signal intensity between the corresponding pixels. For example, in a case, for example, wherein the tissue state of the diseased portion improves (cancerous to normal), the difference is a negative value, and when the tissue state degenerates (e.g. precancerous to cancerous), the difference is a positive value, by assigning green to the negative values and red to the positive values for the pseudo color display, it becomes easy for the diagnostician to recognize the change in the tissue state. Alternatively, the negative values can be green, 0 can be assigned yellow, and positive values assigned red to reflect the contiguous change in the pseudo color display.

As elucidated in the forgoing explanation, according the endoscope apparatus of the present invention: first, the reference image data is subjected to a form correction process so that the form of each respective area delimited by three marks within the reference image data and the form of each respective area delimited by three marks within the comparison image data become substantially equal; next, the reference image data is subjected to a rotation correction process so that the inter-mark orientation of the reference image data and the inter-mark orientation of the comparison image data becomes substantially equal to form a corrected reference image data; whereby, when the corrected reference image data and the comparison image data are displayed on a monitor or the like, because the display state of the image of the vicinity of the diseased portion 11 displayed in the corrected reference image 26' and the display state of the diseased portion 16 displayed in the comparison image are substantially equal, comparison of both images becomes easy, and the diagnostic efficiency in performing a comparison diagnosis is improved.

Further, because each mark is formed of a bio-adhesive containing fluorophores, the correcting portion 241 of the controller 240 can easily recognize the mark image data within the fluorescence image data. Further, it becomes easy to recognize the mark image data when the corrected reference image data and the comparison image data are displayed on the monitor.

Still further, if the superposed display mode is selected, the comparison diagnosis can be performed by observing a single image, whereby the diagnostic efficiency is improved. Further, if the outline superposed display mode is selected, visual confirmation of the size variance of diseased tissue with the passage of time is facilitated, and the diagnostic efficiency of the comparative diagnosis is further improved. If the difference display mode is selected, because it can be easily recognized whether the tissue state of the diseased portion has improved or degenerated with the passage of time, the diagnostic efficiency of the comparison diagnosis can be even further improved.

Note that when the comparison image 27 has been obtained, it is possible to perform only one of either the form correction process or the rotation correction process, according to necessity. Further, according to the current embodiment, although the first mark 21 through the fifth mark 25 have been used, the present invention is not limited thereto; so long as three or more marks are used, any number of marks is possible. If the number of marks is few, the operation of performing the correction processing becomes simple, and can be performed in a short time. If the number of marks is large, although the correction processing becomes complicated, the distortions within small areas can be corrected, and the degree of correction improved.

Note that although standard images have not been compared according to the current embodiment, standard images can be processed in the same manner as fluorescence images, or according to the comparison operation described in the first embodiment.

Further, although according to each embodiment the reference image data has been subjected to the correction processes to render the display state of the reference image data and the comparison image data substantially equal, the present invention is not limited thereto; an endoscope apparatus that subjects the comparison image to the correction processes, or an endoscope apparatus that subjects both the reference image data and the comparison image data to the correction processes are possible variations. Still further, when superposing the image data, the comparison image can be made transparent or the outline image data can be extracted from the comparison image data and superposed on the corrected reference image data. In addition, a brightness correction process can be further performed as required.

Still further, in the side-by-side display mode, two images are displayed side by side on the same monitor; however, two monitors can be provided, and each image displayed on a separate monitor. Note that when two monitors are provided and the corrected reference image and the comparison image are each displayed on a respective monitor, it is preferable that one of the two images be subjected to a position correction process so that the center point of the area enclosed by all of the marks of the corrected reference image and the center point of the area enclosed by all of the marks of the comparison image becomes substantially equal; whereby, the diagnostic efficiency can be improved a level further by displaying at the same position on each monitor the respective area enclosed by all marks within each respective image.

Note that according to each of the embodiments, a still or moving image can be used as the comparison image. If a moving image is used as the comparison image, a high speed controller is required; however, by sequentially displaying in real time the corrected reference image and for the comparison image, the comparison diagnosis can be conducted without interrupting the operation of the endoscope apparatus.

What is claimed is:

1. An endoscope apparatus, comprising:
a light emitting source for projecting light onto an observation area, and an imaging means for obtaining image data based on the reradiated light emitted from the observation area upon the irradiation thereof by the light projected from the light source, further comprising:

a memory means for storing, as first image data, image data obtained by projecting light onto an observation area to which a first mark and a second mark differing from said first mark have been applied;

a magnification correcting means for comparing the first image data stored in said memory means to second image data, which has been obtained after the passage of a predetermined period of time following the obtainment of said first image data, by projecting the light onto the observation area to which the first mark and the second mark have been attached, and subjecting at least one of the first image data and the second image data to a magnification correction process so that the distance between the first mark image data and the second mark image data within the first image data is substantially equal to the distance between the first mark image data and the second mark image data within the second image data; and a diagnostic image forming means for forming a diagnostic image by performing a computational process between the two images that have been subjected to the correction processing, wherein said diagnostic image forming means judges, based on at least one of the two correction processed image data, the region of the diseased portion within said image data and forms an outline image data composed of the outline of the judged diseased region, and superposes said outline image data over the other of the two correction processed image data to form outline superposed diagnostic image data.

2. An endoscope apparatus as defined in claim 1, wherein:
the light source is a means for projecting an excitation light having a wavelength in the 400–420 nm range onto the observation area, and
the image obtaining means is a means for obtaining a fluorescence image of the fluorescence emitted from the observation area upon the irradiation thereof by the excitation light.

3. The endoscope apparatus as defined in claim 2, wherein the first mark and the second mark are formed by a bio-adhesive containing fluorophores.

4. The endoscope apparatus as defined in claim 1, wherein the first mark and the second mark are formed by a bio-adhesive.

5. An endoscope apparatus, comprising:
a light emitting source for projecting light onto an observation area, and an imaging means for obtaining image data based on the reradiated light emitted from the observation area upon the irradiation thereof by the light projected from the light source, further comprising:

a memory means for storing, as first image data, image data obtained by projecting light onto an observation area to which a first mark and a second mark differing from said first mark have been applied;

an orientation correcting means for comparing the first image data stored in said memory means to second image data, which has been obtained after the passage of a predetermined period of time following the obtainment of said first image data, by projecting the light onto the observation area to which the first mark and the second mark have been attached, and subjecting at least one of the first image data and the second image data to a rotation correction process so that the orientation of the second mark image data with respect to the first mark image data within the first image data is substantially equal to the orientation of the second mark image data with respect to the first mark image data within the second image data; and a diagnostic image forming means for forming a diagnostic image by performing a computational process between the two images that have been subjected to the correction processing, wherein said diagnostic image forming means judges, based on at least one of the two correction processed image data, the region of the diseased portion within said image data and forms an outline image data composed of the outline of the judged diseased region, and superposes said outline image data over the other of the two correction processed image data to form outline superposed diagnostic image data.

6. An endoscope apparatus as defined in claim 5, wherein:

the light source is a means for projecting an excitation light having a wavelength in the 400–420 nm range onto the observation area, and the image obtaining means is a means for obtaining a fluorescence image of the fluorescence emitted from the observation area upon the irradiation thereof by the excitation light.

7. The endoscope apparatus as defined in claim 6, wherein the first mark and the second mark are formed by a bio-adhesive containing fluorophores.

8. The endoscope apparatus as defined in claim 5, wherein the first mark and the second mark are formed by a bio-adhesive.

9. An endoscope apparatus, comprising:

a light emitting source for projecting light onto an observation area, and an imaging means for obtaining image data based on the reradiated light emitted from the observation area upon the irradiation thereof by the light projected from the light source, further comprising:

a memory means for storing, as first image data, image data obtained by projecting light onto an observation area including a specified area delimited by a first mark, a second mark, and a third mark;

a form correcting means for comparing the first image data stored in said memory means to second image data obtained by projecting the light onto said observation area including the specified area after the passage of a predetermined period of time from the obtainment of said first image data, and subjecting at least one of the specified area image data of the first image data and the specified area image data of the second image data to a form correcting process so that the form of the specified area within the first image data is substantially equal to the form of the specified area within the second image data; and a diagnostic image forming means for forming a diagnostic image by performing a computational process between the two images that have been subjected to the correction processing, wherein said diagnostic image forming means judges, based on at least one of the two correction processed image data, the region of the diseased portion within said image data and forms an outline image data composed of the outline of the judged diseased region, and superposes said outline image data over the other of the two correction processed image data to form outline superposed diagnostic image data.

10. An endoscope apparatus as defined in claim 9, wherein:

the light source is a means for projecting an excitation light having a wavelength in the 400–420 nm range onto the observation area, and the image obtaining means is a means for obtaining a fluorescence image of the fluorescence emitted from the observation area upon the irradiation thereof by the excitation light.

11. The endoscope apparatus as defined in claim 10, wherein the first mark and the second mark are formed by a bio-adhesive containing fluorophores.

12. The endoscope apparatus as defined in claim 9, wherein the first mark and the second mark are formed by a bio-adhesive.

13. An endoscope apparatus, comprising:

a light emitting source for projecting light onto an observation area, and an imaging means for obtaining image data based on the reradiated light emitted from the observation area upon the irradiation thereof by the light projected from the light source, further comprising:

a memory means for storing, as first image data, image data obtained by projecting light onto an observation area including a specified area delimited by a first mark, a second mark, and a third mark;

a form correcting means for comparing the first image data stored in said memory means to second image data obtained by projecting the light onto said observation area including the specified area after the passage of a predetermined period of time from the obtainment of said first image data, and subjecting at least one of the specified area image data of the first image data and the specified area image data of the second image data to a form correcting process so that the form of the specified area within the first image data is substantially equal to the form of the specified area within the second image data;

a rotation correcting means for subjecting at least one of the specified area image data within the first image data and the specified area image data within the second image data to a rotation correcting process so that the orientation of the second mark image data with respect to the first mark image data within the first image data that has been subjected to the form correction processing substantially matches the orientation of the second mark image data with respect to the first mark image data within the second image data that has been subjected to the form correction processing; and a diagnostic image forming means for forming a diagnostic image by performing a computational process between the two images that have been subjected to the correction processing, wherein said diagnostic image forming means judges, based on at least one of the two correction processed image data, the region of the diseased portion within said image data and forms an outline image data composed of the outline of the judged diseased region, and superposes said outline image data over the other of the two correction processed image data to form outline superposed diagnostic image data.

14. An endoscope apparatus as defined in claim 13, wherein:

the light source is a means for projecting an excitation light having a wavelength in the 400–420 nm range onto the observation area, and the image obtaining means is a means for obtaining a fluorescence image of the fluorescence emitted from the observation area upon the irradiation thereof by the excitation light.

* * * * *